(12) United States Patent
Mizoguchi et al.

(10) Patent No.: US 8,425,838 B2
(45) Date of Patent: Apr. 23, 2013

(54) FILTER MEMBER AND OXYGENATOR USING SAME

(75) Inventors: Kazuhiro Mizoguchi, Fujinomiya (JP); Eiji Kato, Fujinomiya (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 426 days.

(21) Appl. No.: 11/727,608

(22) Filed: Mar. 27, 2007

(65) Prior Publication Data

US 2007/0231203 A1 Oct. 4, 2007

(30) Foreign Application Priority Data

Mar. 28, 2006 (JP) ................. 2006-089283

(51) Int. Cl.
*A61M 1/00* (2006.01)
*A61M 1/14* (2006.01)
*A61M 1/16* (2006.01)
*A61M 1/18* (2006.01)
*A61M 1/34* (2006.01)
*A61M 37/00* (2006.01)

(52) U.S. Cl.
USPC ............ 422/48; 422/44; 422/45; 604/4.01; 604/5.01; 604/6.09; 604/6.14

(58) Field of Classification Search ............ 210/321.74, 210/321.76, 321.78, 321.79, 321.8, 321.81, 210/321.84, 321.87, 321.88, 321.89, 455, 210/4; 261/DIG. 28; 422/45, 46, 48; 604/6.09, 604/6.13, 6.14; 95/45, 54; 96/7, 10

See application file for complete search history.

(56) References Cited

U.S. PATENT DOCUMENTS

| 3,656,513 | A | * | 4/1972 | Evans et al. ................ 138/141 |
| 3,736,641 | A | * | 6/1973 | Fosdick ..................... 29/896.62 |
| 3,807,958 | A | * | 4/1974 | Brumfield et al. ............. 422/46 |
| 4,101,423 | A | * | 7/1978 | Merrill et al. ............. 210/494.1 |
| 4,157,965 | A | * | 6/1979 | Raible ......................... 210/305 |

(Continued)

FOREIGN PATENT DOCUMENTS

| EP | 0 049 461 A2 | 4/1982 |
| EP | 0 306 613 A1 | 3/1989 |
| EP | 1 618 906 A1 | 1/2006 |

OTHER PUBLICATIONS

Online encyclopedia article "Warp (weaving)" accessed Monday, Jul. 13, 2009. http://en.wikipedia.org/wiki/Warp_(weaving).*

(Continued)

*Primary Examiner* — Patricia Bianco
*Assistant Examiner* — Adam Marcetich
(74) *Attorney, Agent, or Firm* — Buchanan Ingersoll & Rooney PC

(57) ABSTRACT

A filter member used in an oxygenator is constructed to provide improved contact with a hollow fiber membrane bundle and to capture bubbles contained in blood. The filter member possesses elasticity at least in the circumferential direction to allow the inner circumference of the filter member to be increased from a natural non-expanded state prior to placement on the hollow fiber membrane bundle to an expanded state in which the inner circumference of the filter member is increased when placed on the hollow fiber membrane bundle. The filter member is constructed to satisfy the condition $0.5 \leq L2/L1 < 1$, wherein L1 represents the outer circumference of the hollow fiber membrane bundle and L2 represents the inner circumference of the filter member in the natural non-expanded state.

13 Claims, 9 Drawing Sheets

U.S. PATENT DOCUMENTS

| | | | |
|---|---|---|---|
| 4,290,987 A * | 9/1981 | Soehngen et al. | 264/41 |
| 4,297,318 A * | 10/1981 | Raible | 422/46 |
| 4,300,277 A * | 11/1981 | Clark | 29/450 |
| 4,396,584 A * | 8/1983 | Burgess et al. | 422/310 |
| 4,401,564 A * | 8/1983 | Epper et al. | 210/150 |
| 4,530,809 A * | 7/1985 | Shindo et al. | 264/210.7 |
| 4,541,981 A * | 9/1985 | Lowery et al. | 264/209.1 |
| 4,572,724 A * | 2/1986 | Rosenberg et al. | 96/6 |
| 4,689,058 A * | 8/1987 | Vogt et al. | 96/135 |
| 4,698,207 A * | 10/1987 | Bringham et al. | 422/46 |
| 5,001,819 A * | 3/1991 | Harrop | 29/33 D |
| 5,013,439 A * | 5/1991 | Fisher et al. | 210/500.23 |
| 5,015,379 A * | 5/1991 | Drori | 210/411 |
| 5,039,413 A * | 8/1991 | Harwood et al. | 210/457 |
| 5,124,127 A * | 6/1992 | Jones et al. | 422/46 |
| RE34,110 E * | 10/1992 | Opie et al. | 600/128 |
| 5,230,726 A * | 7/1993 | Smith et al. | 55/487 |
| 5,297,591 A * | 3/1994 | Baurmeister | 139/383 R |
| 5,460,721 A * | 10/1995 | Goodwin | 210/494.1 |
| 5,578,267 A * | 11/1996 | Cosentino et al. | 422/46 |
| 5,770,149 A * | 6/1998 | Raible | 422/46 |
| 5,800,525 A * | 9/1998 | Bachinski et al. | 623/1.1 |
| 5,858,015 A * | 1/1999 | Fini | 604/403 |
| 6,139,757 A * | 10/2000 | Ohmura et al. | 210/797 |
| 6,503,451 B2 | 1/2003 | Ikeda et al. | |
| 6,540,953 B1 * | 4/2003 | Lee et al. | 264/413 |
| 6,723,283 B2 * | 4/2004 | Ghelli et al. | 422/45 |
| 7,033,497 B1 * | 4/2006 | Yamaguchi et al. | 210/315 |
| 2001/0033813 A1 * | 10/2001 | Filho et al. | 422/307 |
| 2002/0022860 A1 * | 2/2002 | Borillo et al. | 606/200 |
| 2002/0039543 A1 * | 4/2002 | Ikeda et al. | 422/48 |
| 2002/0050036 A1 * | 5/2002 | Perala et al. | 28/142 |
| 2002/0180082 A1 * | 12/2002 | Chandavasu et al. | 264/41 |
| 2006/0016743 A1 * | 1/2006 | Ogihara et al. | 210/321.89 |
| 2006/0142845 A1 * | 6/2006 | Molaei et al. | 623/1.22 |
| 2006/0149314 A1 * | 7/2006 | Borillo et al. | 606/200 |

OTHER PUBLICATIONS

Online encyclopedia article "Warp (weaving)" accessed Mar. 24, 2010. http://en.wikipedia.org/wiki/Warp_(weaving).*
U.S. Appl. No. 11/654,599, filed Jan. 18, 2007, Ogihara.
U.S. Appl. No. 11/655,126, filed Jan. 19, 2007, Ogihara et al.
U.S. Appl. No. 11/179,743, filed Jul. 13, 2005, Ogihara et al.
*European Search Report.
Search Report dated Dec. 30, 2009 issued in the corresponding European Patent Application No. 09170652.3.

* cited by examiner

FILTER MEMBER AND OXYGENATOR USING SAME

TECHNICAL FIELD

The present invention generally pertains to medical devices. More particularly, the present invention relates to a filter member and an oxygenator incorporating a filter member.

BACKGROUND DISCUSSION

U.S. Pat. No. 6,503,451 discloses an oxygenator constructed for gas exchange that utilizes a multiplicity of hollow fiber membranes. This oxygenator includes a housing, a hollow fiber membrane bundle received in the housing, blood inlet and outlet ports, and gas inlet and outlet ports. The oxygenator effects gas exchange (i.e., oxygenation and carbon-dioxide removal) between blood and gas through the hollow fiber membranes.

The construction of this oxygenator makes it susceptible to the possibility that bubbles will become mingled with the blood passing through the blood inlet port. In such a case, it would be desirable to remove the bubbles by virtue of the hollow fiber membrane bundle.

However, the hollow fiber membrane bundle is not fabricated with the intention of removing bubbles, but rather is designed for efficient gas exchange. Hence, the hollow fiber bundle is not well suited to being able to sufficiently effect bubble removal. Thus, it is possible that bubbles remaining in the blood exiting through the blood outlet port will be conveyed downstream of the oxygenator. For this reason, it is known to use an arterial filter for bubble removal on the arterial line from the oxygenator to the patient.

SUMMARY

According to one aspect, an oxygenator comprises a housing, a hollow fiber membrane bundle comprised of a plurality of gas-transmissive hollow fiber membranes each possessing a lumen, a gas inlet port communicating with the lumens of the hollow fiber membranes to introduce an oxygen-containing gas into the lumens, a gas outlet port communicating with the lumens of the hollow fiber membranes, a blood inlet port communicating with a blood flow path that is exterior of the hollow fiber membranes in the housing, a blood outlet port communicating with the blood flow path, and a filter member adapted to be positioned in the housing in surrounding relation to the outer peripheral surface of the hollow fiber membrane bundle. The filter member possesses circumferential elasticity allowing the inner circumference of the filter member to be increased from a natural non-expanded state prior to placement on the hollow fiber membrane bundle to an expanded state in which the inner circumference of the filter member is increased when placed on the hollow fiber membrane bundle. The inner circumference of the filter member in the natural non-expanded state is less than the outer circumference of the hollow fiber membrane bundle.

In accordance with another aspect, an oxygenator comprises a housing, a hollow fiber membrane bundle positioned in the housing and comprised of a plurality of integrated hollow fiber membranes that are transmissive to gas and that each include a lumen, a gas inlet and a gas outlet respectively positioned upstream and downstream of the lumens of the hollow fiber membranes, a blood inlet and a blood outlet respectively positioned upstream and downstream of a blood passage that is exterior of the hollow fiber membranes, and a cylindrically shaped filter member arranged in close contact with the outer periphery of the hollow fiber membrane bundle and structured with a thin thread. The filter member possesses circumferential elasticity allowing the filter member to be circumferentially expanded when placed on the hollow fiber membrane bundle, and the thin thread comprising the filter member is arranged in a direction not coincident with a circumferential direction of the filter member.

According to another aspect, a filter arrangement is configured to be positioned in the housing of an oxygenator and comprises a cylindrically shaped filter member in combination with a hollow fiber membrane bundle comprised of a plurality of integrated hollow fiber membranes that are transmissive to gas. The filter member is configured to be arranged over an outer periphery of the hollow fiber membrane bundle to closely contact the outer periphery of the hollow fiber membrane bundle. The filter member possesses circumferential elasticity allowing the inner circumference of the filter member to be increased from a natural non-expanded state prior to placement on the hollow fiber membrane bundle to an expanded state in which the inner circumference of the filter member is increased when placed on the hollow fiber membrane bundle. With the outer circumference of the hollow fiber membrane bundle being represented by L1 and the inner circumference of the filter member in the natural non-expanded state being represented by L2, the condition $0.5 \leq L2/L1 < 1$ is satisfied.

Another aspect involves an oxygenator comprising a housing, a hollow fiber membrane bundle comprised of a plurality of integrated gas-transmissive hollow fiber membranes each possessing a lumen, a gas inlet port communicating with the lumens of the hollow fiber membranes at an upstream side of the lumens to permit an oxygen-containing gas to be introduced into the lumens, a gas outlet port communicating with the lumens of the hollow fiber membranes at a downstream side of the lumens, a blood inlet port communicating with a blood flow path that is exterior of the hollow fiber membranes in the housing, a blood outlet port communicating with the blood flow path, and a filter member positioned in the housing in surrounding relation to the outer peripheral surface of the hollow fiber membrane bundle. The filter member is comprised of a plurality of threads forming a mesh, and the plurality of threads form an angle other than zero degrees with a plane perpendicular to the longitudinal axis of the filter member so that the filter member possesses circumferential elasticity allowing an inner circumference of the filter member to be increased from a natural non-expanded state prior to placement on the hollow fiber membrane bundle to an expanded state in which the inner circumference of the filter member is increased when placed on the hollow fiber membrane bundle. The outer circumference L1 of the fiber membrane bundle is dimensioned relative to the inner circumference L2 of the filter member in the natural non-expanded state so that $L2/L1 < 1$.

BRIEF DESCRIPTION OF THE DRAWING FIGURES

DETAILED DESCRIPTION

Figure 1:
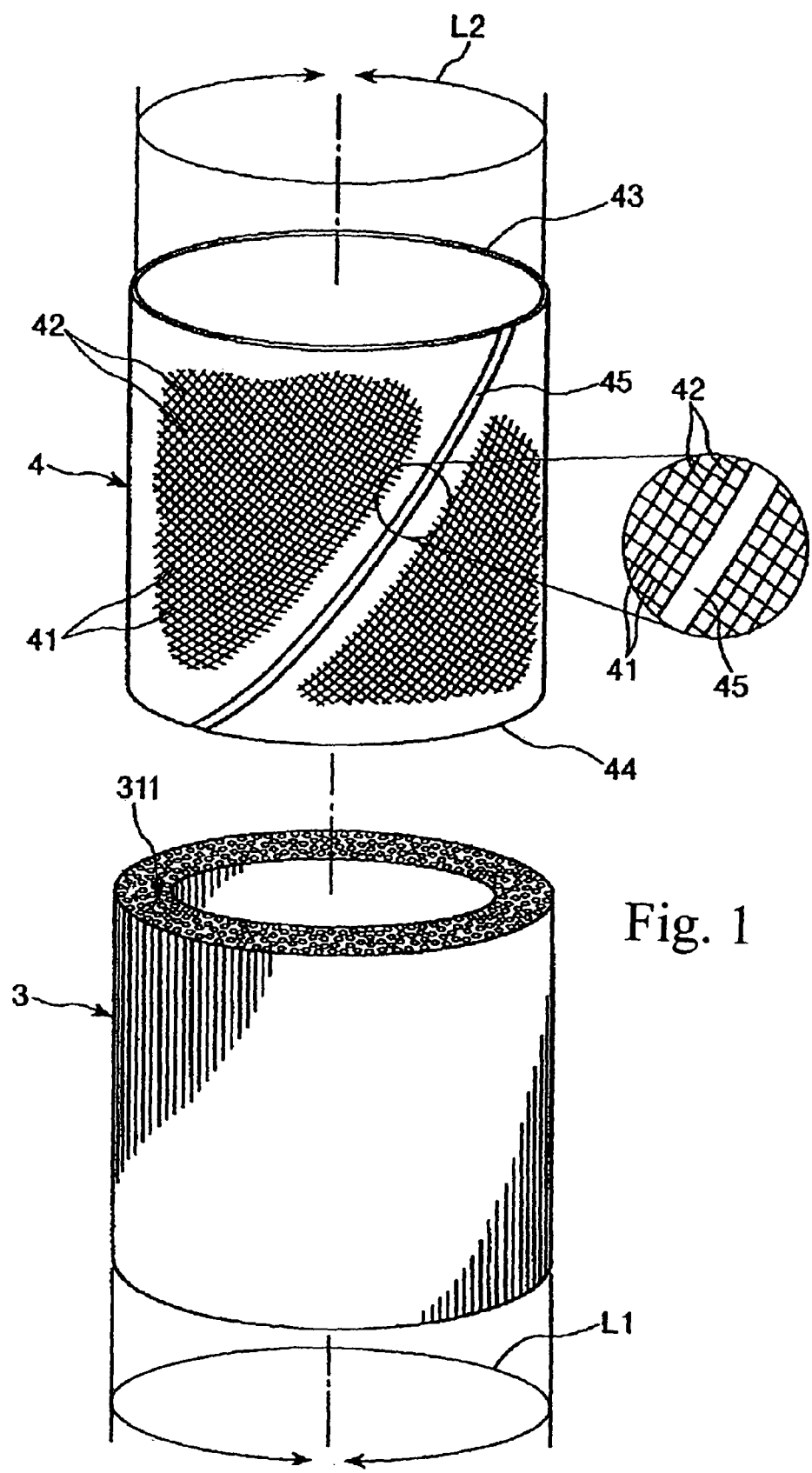
FIG. 1 is a perspective exploded view of an embodiment of a filter member disclosed herein.

FIGS. 2-7 illustrate one embodiment of an oxygenator, including a filter member, as disclosed herein. In the illustrated embodiment shown in FIGS. 2-7, the oxygenator possesses a nearly circular cylindrical exterior form. In the disclosed embodiment, the oxygenator 1 is a heat exchanger-equipped oxygenator which includes an interiorly positioned (centrally positioned) heat exchange part (heat exchanger) 1B that performs heat exchange with blood, and an oxygenator part 1A provided outwardly of the heat exchange part 1B that performs gas exchange with blood.

The oxygenator 1 comprises a housing 2 in which is received the oxygenator 1A and the heat exchange part 1B. Within the housing 2, the heat exchange part 1B is further received in a heat exchanger housing 5. By way of the heat exchanger housing 5, the heat exchange part 1B is fixed at both of its ends to the housing 2.

The housing 2 is comprised of a housing body 21 possessing a circular cylindrical form (hereinafter referred to as "cylindrical housing body"), a first dish-shaped header (upper lid) 22 closing a left-end opening of the cylindrical housing body 21, and a second dish-shaped header (lower lid) 23 closing a right-end opening of the cylindrical housing body 21.

The cylindrical housing body 21, the first header 22 and the second header 23 are formed of a resin material, e.g., polyolefin such as polyethylene or polypropylene, an ester resin (e.g. polyester such as polyethylene terephthalate or polybutylene terephthalate), a styrene resin or polycarbonate, ceramics material of various kinds or a metal material. The first and second headers 22, 23 are secured in a liquid-tight manner to the cylindrical housing body 21 by joining, for example through fusion or an adhesive.

The outer periphery of the cylindrical housing body 21 is formed with a tubular blood outlet port 28. The blood outlet port 28 projects in a direction nearly tangential to the outer peripheral surface of the cylindrical housing body 21.

A blood inlet port 201 and a gas outlet port 27 are formed on first header 22. The blood inlet port 201 and gas outlet port 27 are tubular in form and project from the first header 22.

A gas inlet port 26, a gas outlet port 29, a heating-medium inlet port 202 and a heating-medium outlet port 203 are formed on the second header 23. The gas inlet port 26, gas outlet port 29, heating-medium inlet port 202 and heating-medium outlet port 203 are tubular in form and project from the second header 23.

It is to be understood that the overall shape of the housing 2 need not be perfectly circular cylindrical.

Figure 4:
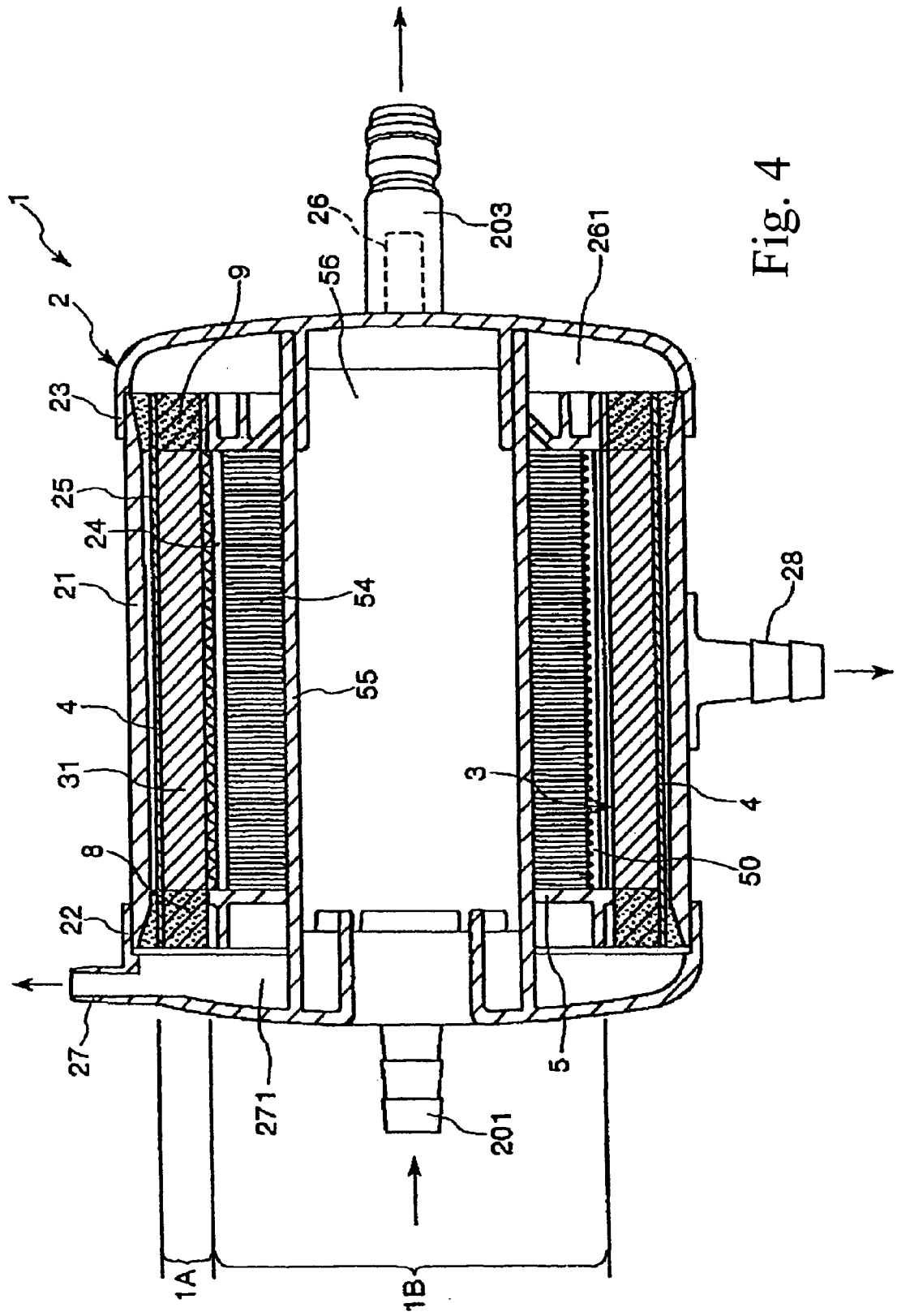
FIG. 4 is a cross-sectional view of the oxygenator taken along the section line IV-IV in FIG. 3.

As shown in FIG. 4, the oxygenator part 1A is received within the housing 2 and possesses a circular cylindrical form extending along the inner peripheral surface thereof. The oxygenator 1A comprises a hollow fiber membrane bundle 3 that is nearly cylindrical in its overall form, and a filter member 4 serving as bubble catching means provided around the hollow fiber membrane bundle 3. The hollow fiber membrane bundle 3 is comprised of a plurality of hollow fiber membranes 311, preferably gas-transmissive hollow fiber membranes.

The hollow fiber membranes 311 and the filter member 4 are fixed at both of their lengthwise ends (axial ends) by way partitioning walls 8, 9 so as to be fixed relative to the inner surface of the cylindrical housing body 21.

Each of the partitioning walls 8, 9 possesses a ring-shaped form as viewed in plan. The partitioning walls 8, 9 are formed from a potting material, e.g., polyurethane or silicone rubber.

Figure 7:
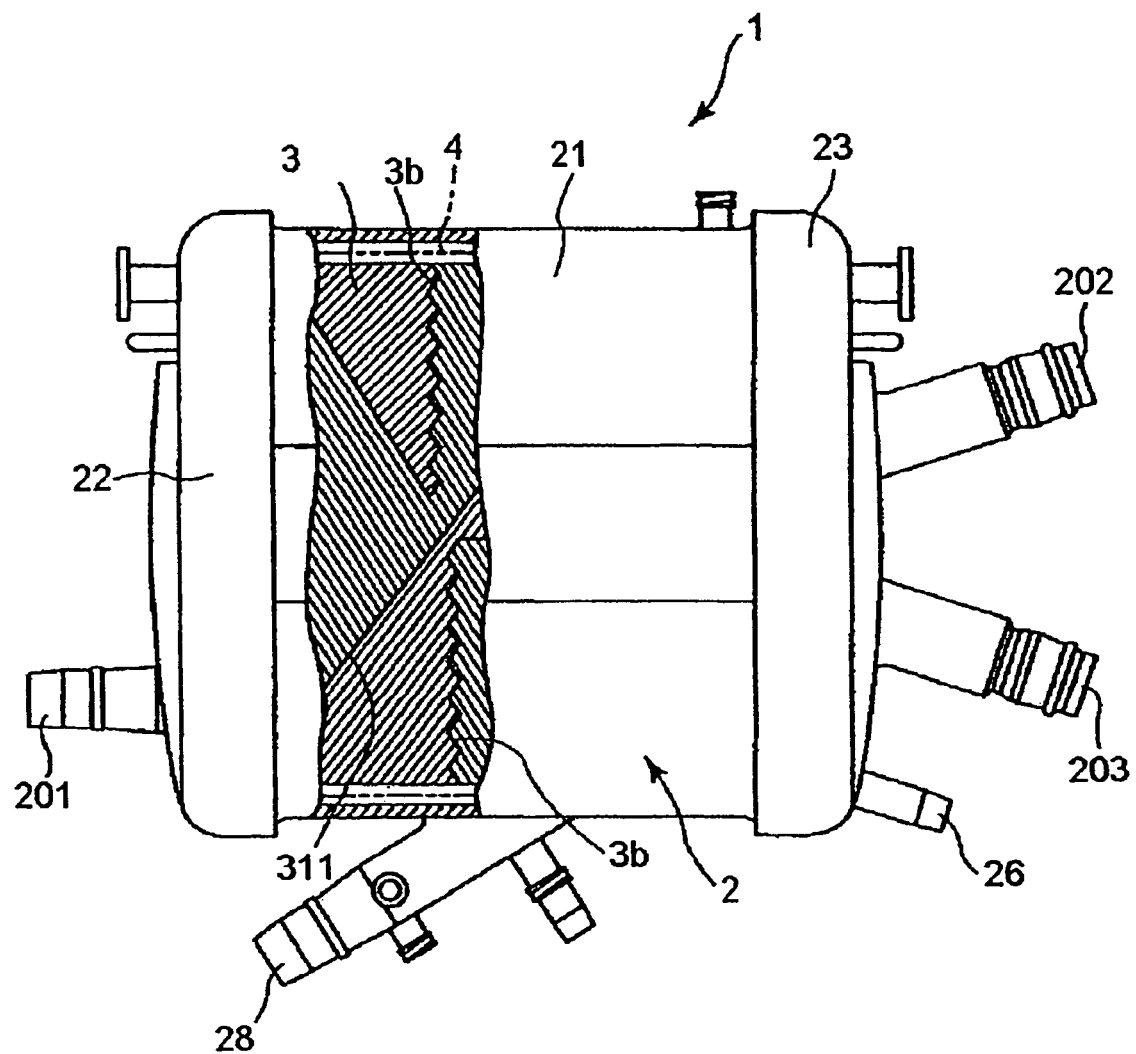
FIG. 7 is a plan view, partly broken away, showing the manner in which the hollow fiber membranes are arranged in the disclosed embodiment.

The hollow fiber membrane bundle 3 can have a construction similar to that described in U.S. Pat. No. 6,503,451. Generally describing the construction of the hollow fiber membrane bundle 3 as shown in FIG. 7, the hollow fiber membranes 311 forming the hollow fiber membrane bundle 3 are spread around the outer periphery of a cylindrical core and are laid out in a multi-layered manner. The hollow fiber membrane bundles can be wound in a reel-type form over the cylindrical core. The hollow fiber membrane bundle 3 has a plurality of crosswinds 3b, where the hollow fiber membranes 311 cross each other at and around the lengthwise central part of the cylindrical core. The crosswinds 3b are arranged so that the radially adjacent i.e., in the thickness-wise direction of the bundle) ones do not overlap one another. Namely, the adjacent crosswinds are located in different positions along the hollow fiber membrane bundle 3 so that a crosswind 3b is not located directly on, in overlapping relation, to another crosswind 3b. This helps avoid the occurrence of a partial projection and a short-circuiting of blood due to overlapping crosswinds 3b.

In the event a projection is partially caused in the outer peripheral surface of the hollow fiber membrane bundle 3 by overlapping crosswinds 3b of the hollow fiber membranes, the contact of the filter member 4 with the hollow fiber membrane bundle may be reduced, or the flow of blood downstream of the filter member 4 may be partially impeded. By reducing the overlap of crosswinds 3b, the possibility of such a problem can be reduced or avoided, thus allowing for good bubble removal capabilities and gas exchange.

Figure 6:
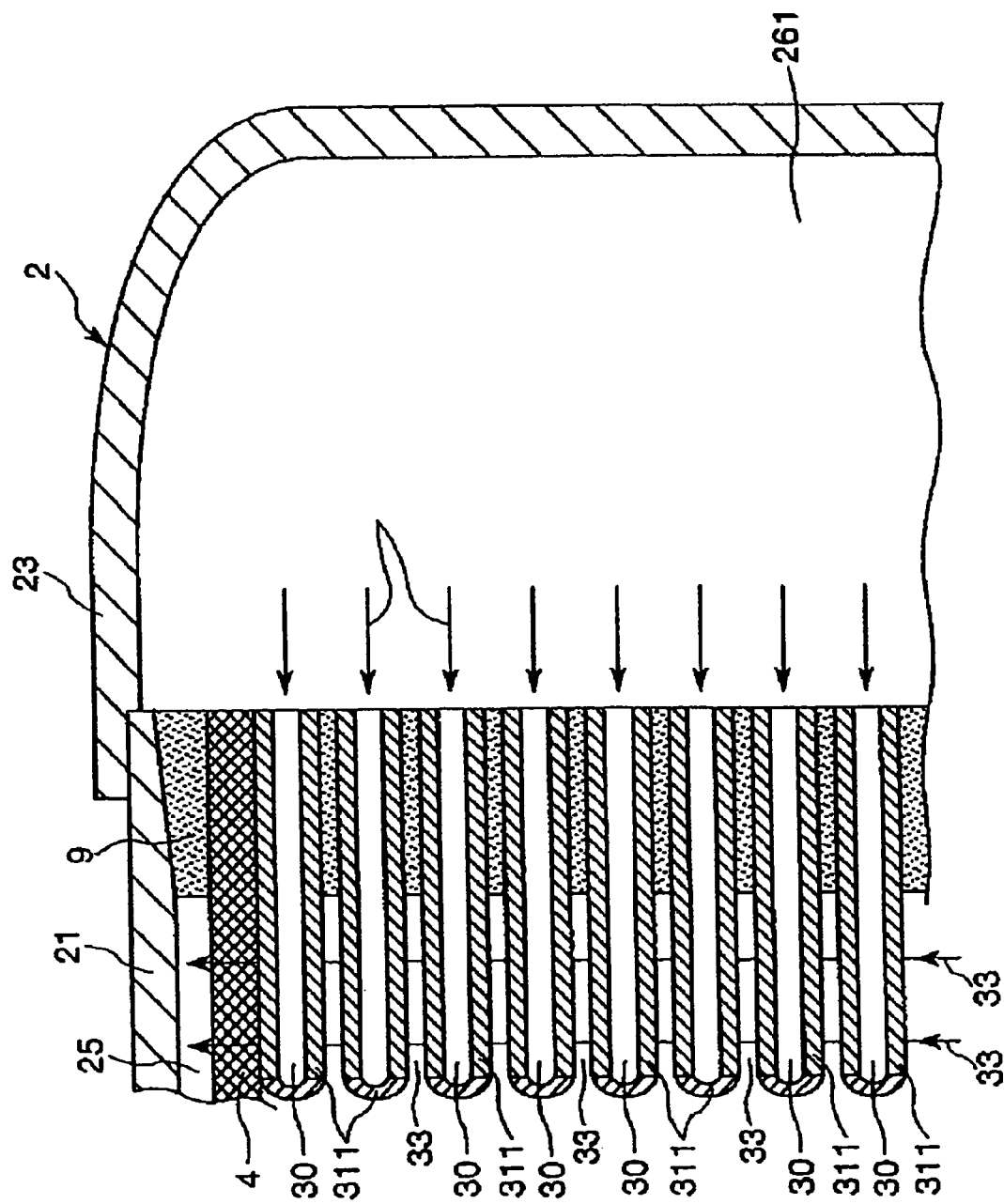
FIG. 6 is an enlarged cross-sectional view of a portion of the oxygenator showing the manner of fixing a hollow fiber membrane and filter member to a partitioning wall.

Within the housing 2, the hollow fiber membranes 311 are exposed between the partitioning walls 8, 9. A blood passage or blood flow path 33 is formed exterior of the hollow fiber membranes 311. That is, the blood passage or blood flow path 33 is arranged at gaps between the hollow fiber membranes 311 as shown in FIG. 6.

A blood inlet space 24 that is circular cylindrical in form exists upstream of the blood passage 33 (i.e., at a position closer to the upstream surface of the hollow fiber membrane bundle 3). The blood inlet space 24 is located between the oxygenator part 1A and the heat-exchange part 1B so that blood from the blood inlet port 201 can enter the blood inlet space 24. The blood inlet space 24 extends around the heat exchange housing 5. That is, the blood inlet space 24 is between the outer peripheral surface of the heat exchange housing 5 and the inner peripheral surface of the hollow fiber membrane bundle 3 as shown in FIG. 4.

Blood which has been heat-exchanged and which enters the blood inlet space 24 is able to flow into the blood inlet space 24 in both the circumferential and lengthwise directions, thus reaching the entirety of the blood inlet space 24. This makes it possible to transfer the blood efficiently from the heat exchange part 1B to the oxygenator part 1A.

A spacer may be provided in the blood inlet space 24 in order to maintain the gap between the heat exchanger housing 5 and the hollow fiber membrane bundle 3.

At a downstream portion of the blood passage 33 (i.e., at a position closer to the downstream surface of the hollow fiber membrane bundle 3), a circular cylindrical gap is formed between the outer peripheral surface of the filter member 4 (described in more detail below) and the inner peripheral surface of the cylindrical housing body 21 to form a blood outlet space 25. A blood outlet is thus provided by the blood outlet space 25 and the blood outlet port 28 communicating with the blood outlet space 25. The blood outlet space 25 provides a space where the blood transmitted the filter member 4 is allowed to flow (particularly in a whirling flow) toward the blood outlet port 28 so that the gas-exchanged blood can smoothly exit to the outside of the housing 2.

The hollow fiber membrane bundle 3, the filter member 4 and the blood passage 33 are present between the blood inlet space 24 and the blood outlet space 25.

Though not especially limited in this regard, the hollow fiber membrane bundle 3 preferably has a thickness (radial dimension in FIG. 4) of approximately 2-50 mm, more preferably approximately 3-30 mm, further preferably approximately 4-20 mm.

The hollow fiber membranes 311 are, in the disclosed embodiment, constituted by porous hollow fiber membranes (porous gas-exchange film). The porous hollow fiber membranes to be used can have an inner diameter of approximately 100-1000 μm, a wall thickness of approximately 5-200 μm and more preferably 10-100 μm, a porosity of approximately 20-80% and more preferably approximately 30-60%, and a pore size (average) of approximately 0.01-5 μm and more preferably approximately 0.01-1 μm.

The material forming the hollow fiber membranes 311 is preferably a hydrophobic polymer material, e.g. polypropylene, polyethylene, polysulfone, polyacrylonitrile, polytetrafluoroethylene or polymethyl pentane. Polyolefin resin is preferred, and polypropylene is more preferred. Pores are preferably formed in a film (a wall of the film) by stretching or solid-liquid phase separation.

The length (effective length) of the hollow fiber membranes 311 is not particularly limited, but is preferably approximately 30-150 mm, more preferably approximately 40-130 mm, and further preferably approximately 50-110 mm.

As mentioned above, the filter member 4 is arranged downstream of the hollow fiber membrane bundle 3 and serves as bubble capture means to capture the bubbles out of the blood. The filter member 4 captures bubbles existing in the blood flowing in the blood passage 33. The captured bubbles enter the lumens (gas passage 30) of the hollow fiber membranes 311 through the multiple pores formed in the walls of the hollow fiber membranes 311. Those bubbles are then discharged through the gas outlet port 27. The filter member 4 is described below in more detail with reference primarily to FIG. 1.

The filter member 4 is formed from a sheet member (hereinafter simply referred to as a "sheet") having a generally rectangular form (e.g., parallelogram). The sheet is rolled up into a cylindrical form or shape (annular form or shape) having ends/edges joined together to form a cylindrical (circular cylindrical) filter member as shown in FIG. 1. The filter member 4 is secured at both of its lengthwise or axial ends 43, 44 (i.e., the upper and lower ends in FIG. 1) respectively by way of the partitioning walls 8, 9 so that the filter member is fixed to the housing 2.

The filter member 4 is positioned relative to the hollow fiber membrane bundle 3 so that the inner peripheral surface of the filter member 4 is in contact with the outer peripheral surface of the hollow fiber membrane bundle 3. The filter member 4 is configured and positioned to cover nearly all of the outer peripheral surface of the hollow fiber membrane bundle 3. With this arrangement, the effective area of the filter member 4 is increased to an extent allowing the filter member to fully exhibit the capability of capturing bubbles. In addition, because of the increased effective area of the filter member 4, the filter member 4 can help prevent (suppress) the blood flow from being blocked even if clogging occurs (e.g. adhesion of blood aggregations) in a part of the filter member 4, thus making it possible to continue the operation of the oxygenator 1.

The filter member 4 possesses elasticity at least in the circumferential direction. By virtue of this, when the filter member 4 is fitted onto the outer periphery of the hollow fiber membrane bundle 3, the fiber member 4 achieves a close fit with the outer peripheral surface of the hollow fiber membrane bundle 3.

The filter member 4 is preferably constructed relative to the hollow fiber membrane bundle 3 so that the inner circumference of the filter member 4 in the natural state prior to placement on the hollow fiber membrane bundle 3 is less than the outer circumference of the hollow fiber membrane bundle. More specifically, the filter member 4 is preferably constructed relative to the hollow fiber membrane bundle 3 to satisfy the relationships described below. If the outer periphery (outer circumference) of the hollow fiber membrane bundle 3 over which the filter member 4 is fitted is represented by the length L1 as shown in FIG. 1, and the inner periphery (inner circumference) of the filter member 4 in the natural state in which no external force is applied (the state in which the filter member 4 is neither expanded nor contracted circumferentially, hereinafter referred to as the "natural state") is represented by the length L2 as shown in FIG. 1, the filter member 4 is preferably constructed so that the condition $0.5 \leq L2/L1 < 1$ is satisfied, preferably so that the condition $0.55 \leq L2/L1 \leq 0.99$ is satisfied, and more preferably so that the condition $0.93 \leq L2/L1 \leq 0.98$ is satisfied. Thus, $L2/L1 < 1$. The inner circumference of the filter member mentioned above refers to the distance around the inner peripheral surface of the filter member as measured at a plane perpendicular to the longitudinal axis of the filter member, and the outer circumference of the fiber membrane bundle mentioned above refers to the distance around the outer peripheral surface of the fiber membrane bundle as measured at a plane perpendicular to the longitudinal axis of the fiber membrane bundle.

By satisfying this condition, the filter member 4 when fit over the outer periphery of the hollow fiber membrane bundle 3 is positively placed into close contact with the outer peripheral surface of the hollow fiber membrane bundle 3 cooperatively with the circumferential elasticity. As a consequence, the bubbles captured at the filter member 4 are readily excluded through the hollow fiber membrane 311 located immediately nearby the inner (upstream) surface of the filter member 4. Namely, the satisfaction of the condition can enhance the discharge efficiency (removal capability) of the bubbles captured by the filter member 4.

The filter member 4 may be, say, a mesh structure or a woven fabric, a non-woven fabric or a combination thereof. Of these, a mesh structure is preferred, and particularly a screen mesh filter is preferred. This structure makes it possible to catch bubbles more positively and to pass blood easily, thus contributing to providing an oxygenator having relatively high blood processing efficiency and relatively excellent sustainability (i.e., is capable of operating for a relatively long time).

Figure 2:
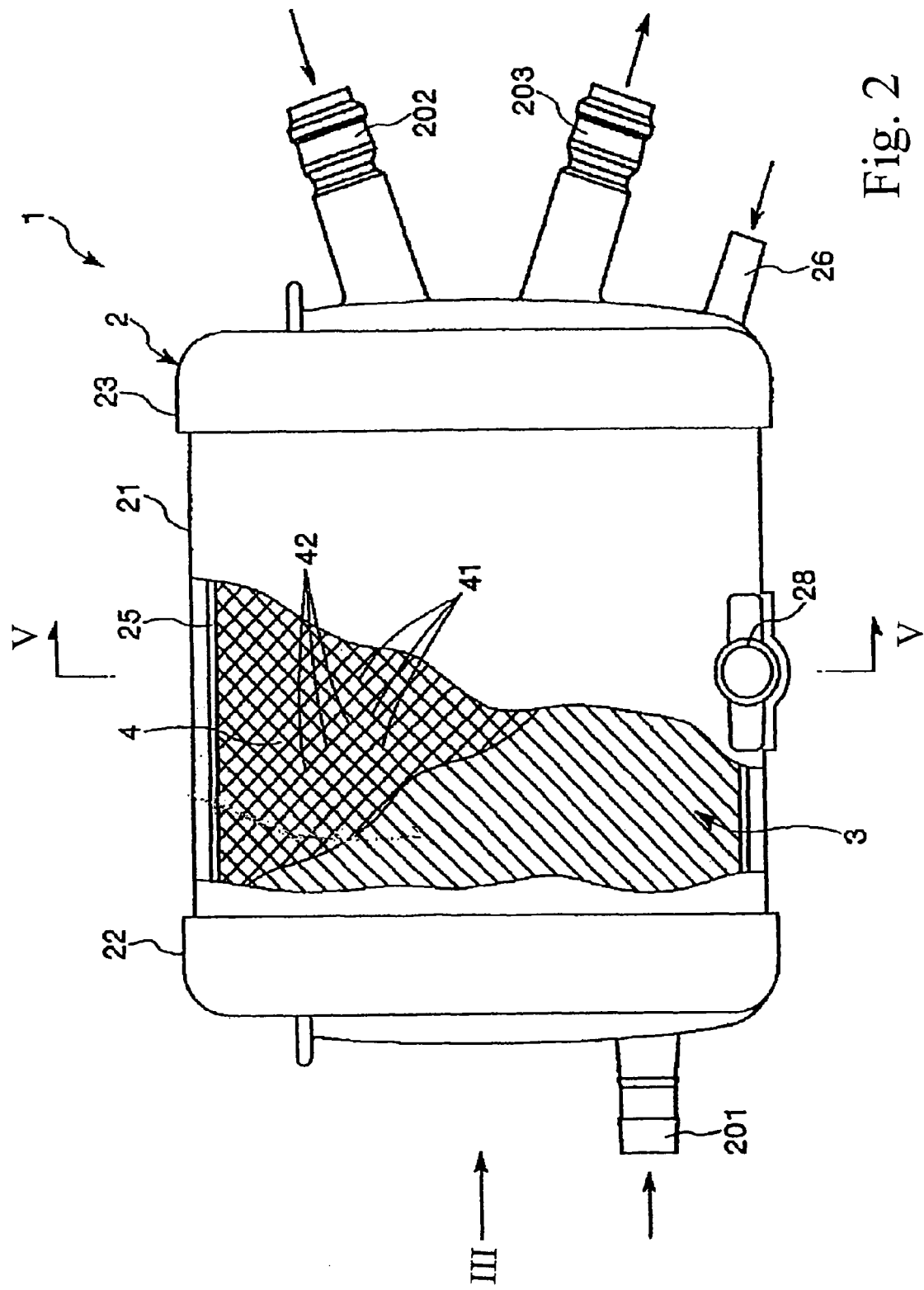
FIG. 2 is a plan view, partly broken away, of an embodiment of an oxygenator disclosed herein.
Figure 3:
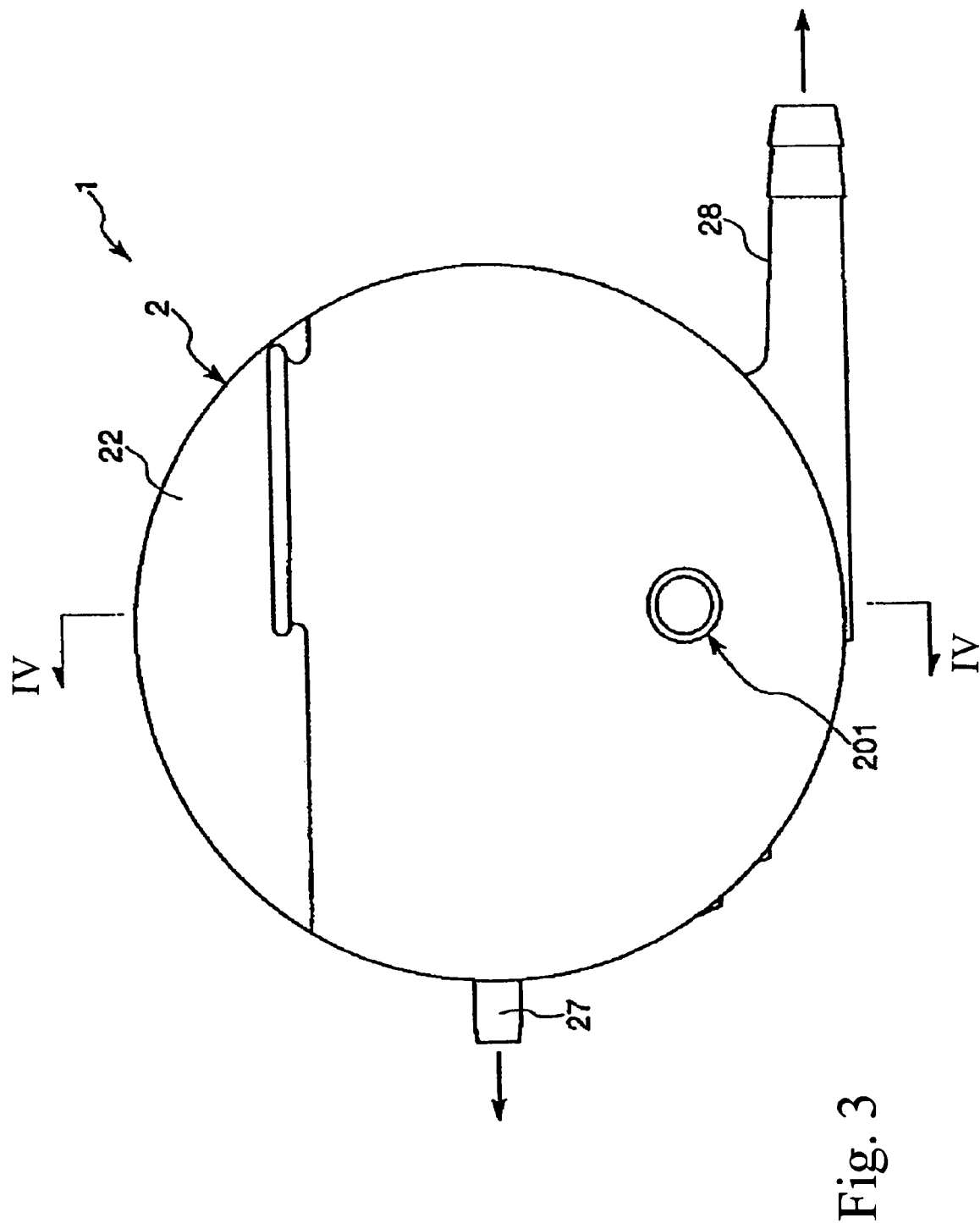
FIG. 3 is a left side view of the oxygenator shown in FIG. 2 as viewed in a direction of arrow III.

Meanwhile, the filter member 4 is preferably formed by a sheet made by crossing a weft thread (thin wire) 41 and a warp thread (thin wire) 42 with each other as generally seen in FIGS. 1 and 2. Such structure includes, by way of example, a woven fabric that is weaved plain with a warp thread 41 and a weft thread 42, a resin-made mesh (including a screen mesh filter) formed by crossing a warp thread (resin-fibrous thin wire) 41 and a warp thread (resin-fibrous thin wire) 42 into a lattice form, and others. Such a structure can capture bubbles positively while allowing blood to relatively easily pass, thus contributing to providing an oxygenator having relatively high blood processing efficiency and relatively excellent sustainability (i.e., is capable of operating for a long time).

The warp thread 41 and the weft thread 42 may be fixed or not fixed at points or areas of intersection (or may movable freely to a certain extent).

When the filter member 4 is a mesh structure as mentioned above, the mesh size is not particularly limited, though is usually preferably 80 μm or smaller, more preferably approximately 15-60 μm, further preferably 20-45 μm. This makes it possible to catch comparatively fine bubbles without increasing the passage resistance to blood, thus providing a relatively high bubble capturing efficiency. Where the filter member 4 is constructed as a sheet made by crossing the warp thread 41 and the weft thread 42, it is preferable that the warp thread 41 and the weft thread 42 do not extend in a direction that is the same as the circumferential direction (extending direction) of the filter member 4. That is, it is preferable that the warp thread 41 and the weft thread 42 do not extend parallel to a plane that is perpendicular to the longitudinal axis or central axis of the filter member. More specifically, the warp thread 41 and the weft thread 42 are each preferably arranged in a direction that is inclined (i.e., forms an angle other than zero degrees) relative to a plane perpendicular to the longitudinal axis or central axis of the filter member. The warp thread 41 and the weft thread 42 are each preferably arranged to form a predetermined angle (e.g., 28-62 degrees) to the plane perpendicular to the longitudinal axis of the filter member. In other words, where the filter member 4 is constructed as a sheet formed by crossing a warp thread 41 and a weft thread 42, its mesh structure (i.e., the mesh openings forming the overall mesh structure) is a quadrilateral, e.g., a square, a rectangle, a rhombus or a parallelogram. The quadrilateral mesh structure has a pair of opposite sides arranged in a direction inclined a predetermined angle (e.g., 28-62 degrees) to the circumferential direction of the filter member 4. Depending upon the expansion and contraction of the filter member 4, the angle of the quadrilateral changes in the mesh corner.

This structure helps contribute to the filter member 4 possessing elasticity (particularly appropriate elasticity) in the circumferential direction while still possessing sufficient strength with a relatively simple construction. Meanwhile, the elasticity is obtained in a rather stable manner. Due to this, tightening force (compression force) applied to the hollow fiber membrane bundle 3 is relatively uniform and stable, contributing to the improvement of bubble-removal capability. Furthermore, such a construction prevents or suppresses the occurrence of wrinkles (wavy concavo-convex) in the sheet at and around the joint (fusion) region 45 of the filter member 4. By the improved contact of the filter member 4 with the hollow fiber membrane bundle 3, it is possible to improve the discharge efficiency of the bubbles captured by the filter member 4 and to help ensure that the blood smoothly flows on the outer periphery (downstream) of the filter member 4, i.e., in the blood outlet space 25.

In the event a wrinkle is formed as mentioned above, the following disadvantage results. First, at the inner periphery (upstream) of the filter member, the bubbles captured by the filter member are liable to stay in a recess of the wrinkle and hence will not be easily removed therefrom. In addition, on the outer periphery (downstream) of the filter member, the wrinkle possibly has a projection contacting the inner surface of the housing, thereby preventing the blood from flowing smoothly (i.e., smooth blood flow within the blood outlet space 25 in this disclosed embodiment). It is this preferable that no wrinkles, or only a few wrinkles, are allowed to occur.

As noted before, the filter member 4 is preferably fabricated by rolling up the sheet into a cylindrical (annular) form and joining the ends or edges thereof together in a strip form. The joint (sealing) 45 between the sheet ends extends over the entire width (vertical dimension in FIG. 1) of the filter member 4, from one end 43 of the filter member 4 to the other end 44 of the filter member 4 as shown in FIG. 1.

In this case, the strip-like joint region 45 preferably extends in a direction inclined at a predetermined angle (e.g. 28-62 degrees) relative to the widthwise (or circumferential) direction of the filter member 4. As described before, when the filter member 4 is fit onto the outer periphery of the hollow fiber membrane bundle 3, the filter member 4 shifts from the natural state to a state in which the filter member 4 is expanded circumferentially and applied with a tension. By positioning or orienting the joint region 45 in a direction inclined relative to the widthwise direction of the filter member 4, the possibility of a wrinkle occurring in the sheet at and around the joint region 45 can be reduced, preferably prevented. This improves the contact of (or places without a gap) the filter member 4 with the outer peripheral surface of the hollow fiber membrane bundle 3. The bubbles, caught at the filter member 4 are relatively easily expelled through the hollow fiber membrane 311 located immediately close to the inner surface of the filter member 4. Namely, the expelling efficiency can be enhanced as to the bubbles captured at the filter member 4.

The joint region 45 is preferably parallel (inclusive of nearly parallel) with the extending direction of the warp thread 41 or weft thread 42 that is inclined relative to the circumferential direction of the filter member 4. Namely, in this embodiment, the junction region 45 is parallel (inclusive of nearly parallel) with the weft thread 42 and perpendicular (inclusive of nearly perpendicular) to the warp thread 41, as shown with magnification in FIG. 1, though the embodiment is not necessarily limited in this way. This can help reduce the possibility of the warp thread 41 or weft thread 42 being puckered, to reduce or prevent such a disadvantage as forming a wrinkle (concavo-convex) in part of the sheet. This improves the contactability of (or places without a gap) the filter member 4 with the outer peripheral surface of the hollow fiber membrane bundle 3, thus relatively easily expelling the bubbles captured at the filter member 4 through the hollow fiber membrane 311 located immediately close to the inner surface of the filter member 4. Namely, the expelling efficiency of the bubble captured at the filter member 4 can be improved.

The joining of the sheet edges to form the joint region 45 is not limited in any particular manner, but is preferably by way of fusion such as thermal fusion, high-frequency fusion or ultrasonic fusion, or adhesion with an adhesive material. This makes it possible to relatively easily fabricate the filter member 4. Moreover, even if the filter member 4, when fit onto the hollow fiber membrane bundle 3, is expanded, the joining region 45 is secured with sufficient joining strength. Accordingly, the joining region 45 is prevented from being stripped off in part thereof and the joining state is maintained without a gap throughout the entire length of the joining region 45, thus effectively reducing, preferably preventing, the leak of bubbles.

The material forming the filter member 4 (the material of the warp thread 41 and the weft thread 42) can be appropriately selected, say, polyolefin such as polyamide, polyethylene or polypropylene, polyester such as polyethylene terephthalate, or polybutylene terephthalate, polyamide, cellulose, polyurethane, aramid fiber or the like. Of those, one or two can be used in combination (e.g., to make the warp and weft threads 41, 42 in different compositions, make the warp thread 41 and/or the weft thread 42 as a blended fabric, or so on). Particularly, the filter member 4 preferably uses or includes, as its structuring material, any of polyethylene terephthalate, polyethylene, polypropylene, polyamide and polyurethane in respect to an excellent antithrombotic property and clogging generated less.

The filter member 4 preferably also exhibits hydrophilic properties (possesses hydrophilicity). Namely, the filter member 4 itself preferably is made of a hydrophilic material or the filter member 4 have been subjected to a hydrophilizing processing (e.g. plasma processing). When the blood mingled with bubbles is passing, it is difficult for the bubbles to pass through, thus improving the bubble capture capability at the filter member 4 and helping to positively prevent the bubbles from going out through the blood outlet port 28. In addition, blood passage resistance is reduced at the filter member 4, thus improving the processing efficiency of blood.

The filter member 4 may be comprised of one sheet (particularly, a mesh structure like a screen mesh filter) or may be comprised of two or more sheets.

As mentioned previously, a gap (i.e., a blood outlet space 25) is formed downstream of the filter member 4, between the outer peripheral surface of the filter member 4 and the inner peripheral surface of the housing 2. This helps suppress the filter member 4 from directly (closely) contacting the inner surface of the housing 2. Thus, the blood passing the filter member 4 is allowed to relatively easily flow down the blood outlet space 25 or move in a whirling manner, and then flow relatively smoothly toward the blood outlet port 28.

A spacer may be provided in the blood outlet space 25 to help maintain or keep the gap between the filter member 4 and the housing 2.

With the filter member 4 as described above, even where bubbles exist in the blood flowing in the blood passage 33, such bubbles can be captured with quite good efficiency. The bubbles captured by the filter member 4 are expelled and removed through the hollow fiber membranes 311 located upstream of the filter member 4. Therefore, the bubbles are prevented from exiting through the blood outlet port 28. In this case, because of the close contact between the filter member 4 and the hollow fiber membrane bundle 3, bubbles tend not to stay between the filter member 4 and the hollow fiber membrane bundle 3. The bubbles captured at the filter member 4 can be expelled relatively swiftly as much as possible.

The hollow fiber membranes 311 each have a lumen forming a gas passage 30 through which an oxygen-containing gas is adapted to flow. The gas inlet port 26 and the gas inlet chamber 261 constitute a gas inlet located upstream of the gas passage 30 while the gas outlet port 27 and the gas outlet chamber 271 constitute a gas outlet located downstream of the gas passage 30. The gas passage 30 serves also as a passage that removes the bubbles captured at the filter 4.

As described before, the heat exchange part (heat exchanger) 1B is positioned inside the oxygenator part 1A. The heat exchange part 1B comprises a heat exchanger housing 5. The heat exchanger housing 5 is nearly circularly cylindrical in form, forming a blood chamber 50 therein. On the right side of the heat exchanger housing 5, as seen in FIG. 2 for example, there are formed a heating medium inlet port 202 and a heating medium outlet port 203 that are both tubular in form.

Figure 5:
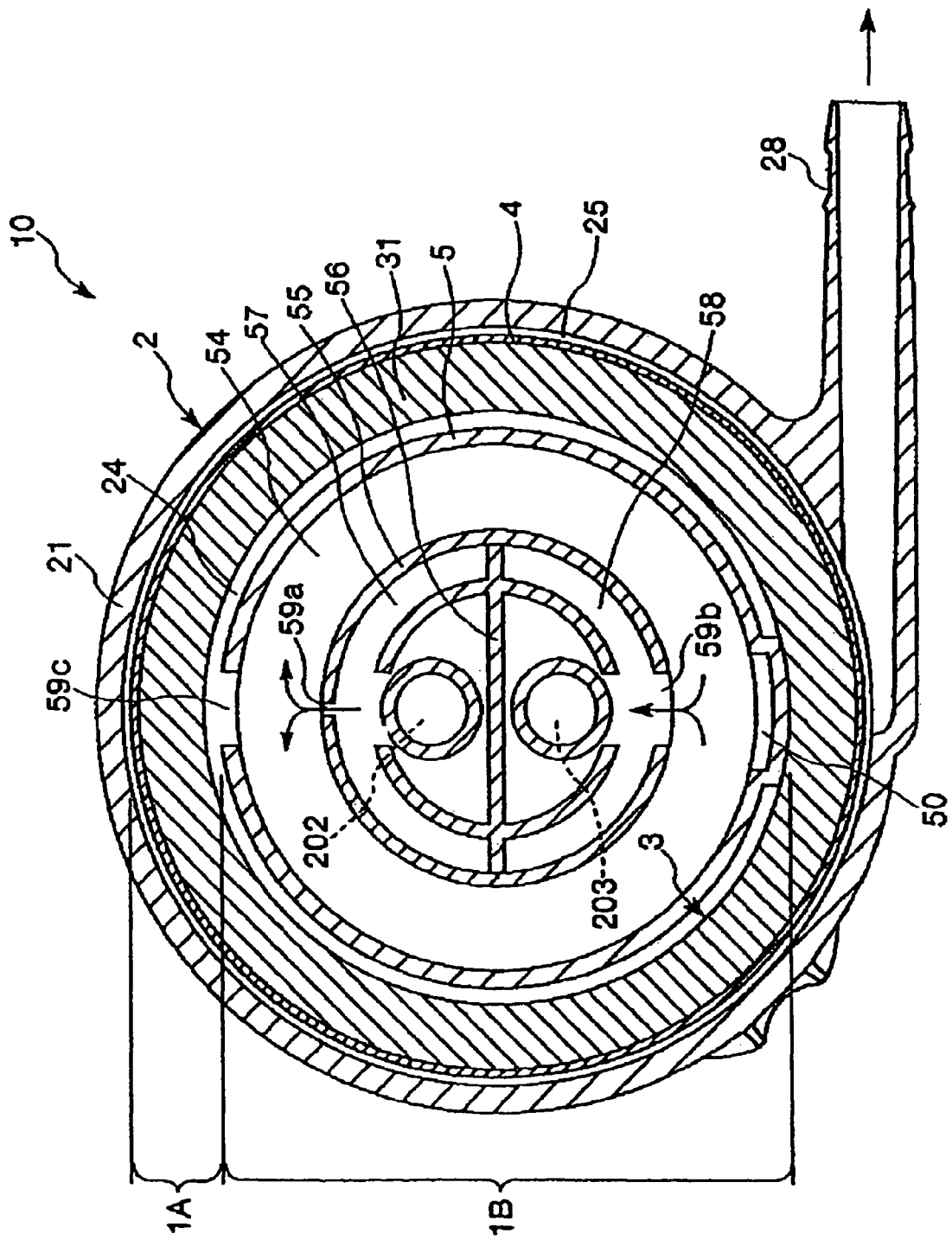
FIG. 5 is a cross-sectional view of the oxygenator taken along the section line V-V in FIG. 2.

As shown in FIGS. 4 and 5, arranged within the heat exchanger housing 5 are a heat exchange element 54 possessing an overall circular cylindrical form, a heating medium chamber-forming member (cylindrical wall) 55 arranged along the inner periphery of the heat exchange element 54 and possessing a circular cylindrical form, and a partitioning wall 56 separating the inner space of the heating medium chamber-forming member 55 into a heating medium inlet chamber 57 and a heating medium outlet chamber 58.

The blood chamber 50 is formed between the outer peripheral surface of the heat exchange element 54 and the inner peripheral surface of the heat exchanger housing 5, allowing the blood to flow. The blood inlet port 201 formed in the first header 22 has a lumen communicating with the blood chamber 50.

The heating medium chamber-forming member 55 serves to form a heating medium chamber that temporarily stores the heating medium at the inside of the heat exchange element 54 and, with the heat exchanger housing 5, helps prevent the cylindrical heat exchange element 54 from deforming.

The heating medium chamber-forming member 55 and the partitioning wall 56 are fixed to the heat exchanger housing 5 by, for example, fusion or bonding through an adhesive. The heating medium chamber-forming member 55 and the partitioning wall 56 may be formed as separate members or as an integral one-piece member.

Openings 59a, 59b penetrate the wall of the heating medium chamber-forming member 55 at diametrically opposite positions in the illustrated embodiment shown in FIG. 5. The opening 59a communicates with the heating medium inlet chamber 57 while the opening 59b communicates with the heating medium outlet chamber 58.

The heat exchange element 54 can be in the form of a bellows-type heat exchange element (bellows tube). The bellows-type heat exchange element 54 comprises a bellows-formed central portion and a cylindrical portion at each axial end. The bellows-formed central portion is comprised of a multiplicity of hollow annular projections that are parallel (inclusive of nearly parallel) to one another so as to form a plurality of closely arranged undulations. The inner diameter of each cylindrical end portion is equal to (inclusive of nearly equal to) the inner diameter of the bellows-formed central portion. The heat exchange element 54 is formed of a metal material such as stainless steel or aluminum, or a resin material such as polyethylene or polycarbonate, for example. It is preferable to use a metal material, such as stainless steel or aluminum for strength considerations and heat exchange efficiency. It is particularly preferable to construct the heat exchange element as a metal-made bellows tube in a corrugated form having a multiplicity of repeating concavo-convex undulations nearly orthogonal to the axis of the heat exchange element 54.

The heat exchanger housing 5, the heating medium chamber-forming member 55 and the partitioning wall 56 can be fabricated of various materials, for example polyolefin such as polyethylene or polypropylene, an ester resin (e.g. polyester such as polyethylene terephthalate, or polybutylene terephthalate), a styrene resin, a resin material such as polycarbonate, various kinds of ceramics material or a metal material.

Set forth below is a description of the flow of the heating medium in the heat exchanging part 1B of the oxygenator 1.

With reference to FIG. 5, the heating medium entering through the heating medium inlet port 202, first flows into the heating medium inlet chamber 57 and then to the outer peripheral side of the heating medium chamber-forming member 55 via the opening 59a, thus spreading over the entire periphery of the heating medium chamber-forming member 55 and entering the multiplicity of recesses or undulations of the bellows-type heat exchange element 54. This heats up or cools down the heat exchange element 54 in contact with the heating medium. Thus, heat exchange (heating or cooling) is effected with the blood entering the blood inlet port 201 and flowing into the blood chamber 50 (on the outer periphery of the heat exchange element 54).

The blood thus heat-exchanged passes through the opening 59c, formed in an upper region of the heat exchanger housing 5, and the blood inlet space 24 in that order, then flows into the housing 2 of the oxygenator part 1A. The blood, entering the blood inlet space 24 spreads our over the entire circumference of the blood inlet space 24 where it flows into the blood passage 33 through various points for gas exchange.

Meanwhile, the heating medium which has been used to perform heating or cooling enters the heating medium outlet chamber 58 through the opening 59b and then exits at the heating medium outlet port 53.

It is to be noted that while the embodiment described above includes the heat exchanging part 1B, the heat exchanging part 1B is not required.

Set forth below is a description of the blood flow in the oxygenator 1 according to this embodiment.

In the oxygenator 1, the blood entering at the blood inlet port 201 flows into the blood chamber 50 (i.e., between the inner surface of the heat exchanger housing 5 and the heat exchange element 54) where it contacts the outer surface of the plurality of hollow annular projections or undulations of the heat exchange element 54, thus effecting heat exchange (heating or cooling). The blood, heat-exchanged in the blood chamber 50, passes through the opening 59c and spreads into the blood inlet space 24. The blood flows downstream (i.e., toward the outer periphery) along the blood passage 33.

Meanwhile, the gas (oxygen-containing gas) supplied through the gas inlet port 26 enters the gas inlet chamber 261 and is distributed from the gas inlet chamber 261 into the gas passages 30 formed by the lumens of the hollow fiber membranes 311. After passing through the gas passages 30, the gas is collected in the gas outlet chamber 271 and allowed to exit at the gas outlet port 27. The blood flowing along the blood passage 33 contacts the surfaces of the hollow fiber membranes 311 so that gas exchange (oxygenation, removal of carbon dioxide) is achieved with the gas flowing through the gas passages 30.

In the event bubbles are present in the blood, such bubbles are captured by the filter member 4 and are not allowed to exit to the downstream side of the filter member 4. The bubbles, captured at the filter member 4, enter the lumens (gas passages 30) of the hollow fiber membranes 311 located upstream of and adjacent to the filter member 4 via the multiplicity of fine pores formed in the material (walls) of the hollow fiber membranes 311. The bubbles entering the lumens of the hollow fiber membranes 311 are discharged at the gas outlet port 29.

The blood thus subjected to gas exchange, and also subjected to bubble removal by virtue of the filter member 4, flows into the blood outlet space 25 and toward the blood outlet port 28, with the blood exiting through the blood outlet port 28.

The oxygenator 1 described above as one embodiment is preferably constructed so that the surfaces which are to contact blood (e.g., the inner surface of the housing 2, the inner surface of the heat exchanger housing 5, the surface of the heating medium chamber-forming member 55, the surface of the partitioning wall 56, the fixed region 7, and the surfaces of the partitioning walls 8, 9 facing the blood passage 33) are antithrombotic. Such an antithrombotic surface can be formed by coating or applying an antithrombotic material onto the surfaces. The antithrombotic material may be heparin, urokinase, HEMA-St-HEMA copolymer, poly-HEMA or the like.

The blood flow rate at the blood inlet port 28 of the oxygenator 1 is not limited to any specific value as it will vary, at least in part, depending upon, for example, the patient's physique and the operational scheme. However, as examples, a blood flow rate of 0.1-2.0 L/min is preferred in an infant or child, a blood flow rate of 2.0-5.0 L/min is preferred for a child in elementary or middle school, and a blood flow rate of 3.0-7.0 L/min is preferred for adults.

The gas flow rate at the gas inlet port 26 is also not particularly limited as it will diff depending upon, for example, the patient's physique and the operational scheme. However, by way of example, a gas flow rate of 0.05-4.0 L/min is preferred for an infant or child, a gas flow rate of 1.0-10.0 L/min is preferred for a child in elementary or middle school, and a gas flow rate of 1.5-14.0 L/min is preferred for an adult.

The oxygen concentration in the gas supplied through the gas inlet port 26 is not limited to a specific value because it will differ depending upon, for example, the metabolic amount of oxygen/carbon-dioxide gas of the patient undergoing the medical procedure. Nevertheless, as an example, the oxygen concentration in the gas can be on the order of 40-100%.

The maximum continuous operation time of the oxygenator 1 will also differ depending upon the patient's condition and the operational scheme. However, a maximum continuous operation time of the oxygenator 1 is usually approximately 2-9 hours. The maximum continuous operation time of the oxygenator 1 will rarely amount to a time as long as nearly 10 hours.

Despite its relatively small size, the oxygenator 1 disclosed here has a relatively high performance, i.e., a relatively high gas exchange capability without outputting bubbles, and also has a relatively excellent sustainability in performance. Accordingly, it can fully cope with a relatively long time of operation, hence being broad in its applications.

Figure 8:
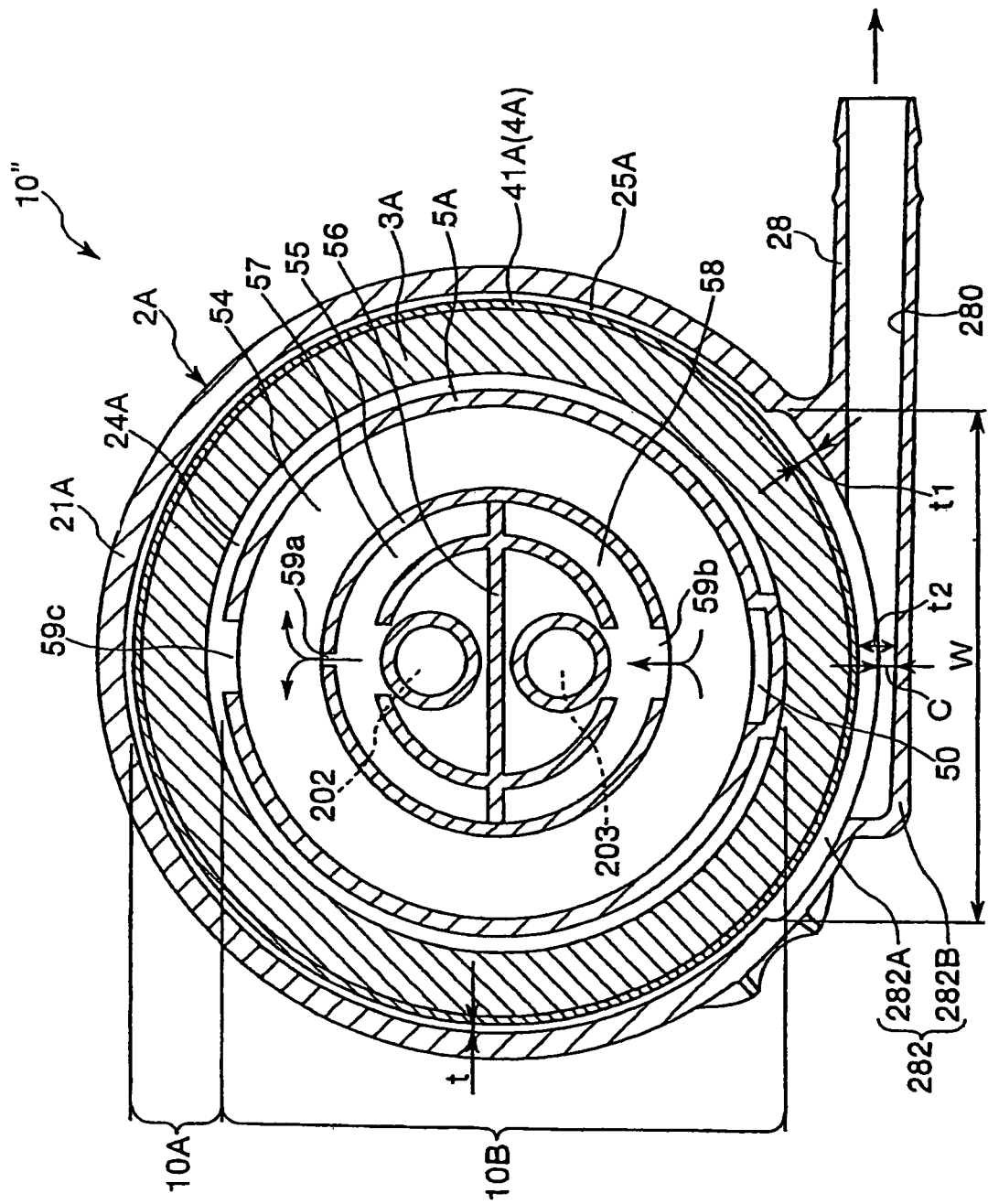
FIG. 8 is a cross-sectional view similar to FIG. 5 illustrating another embodiment of the oxygenator that includes a different housing.
Figure 9:
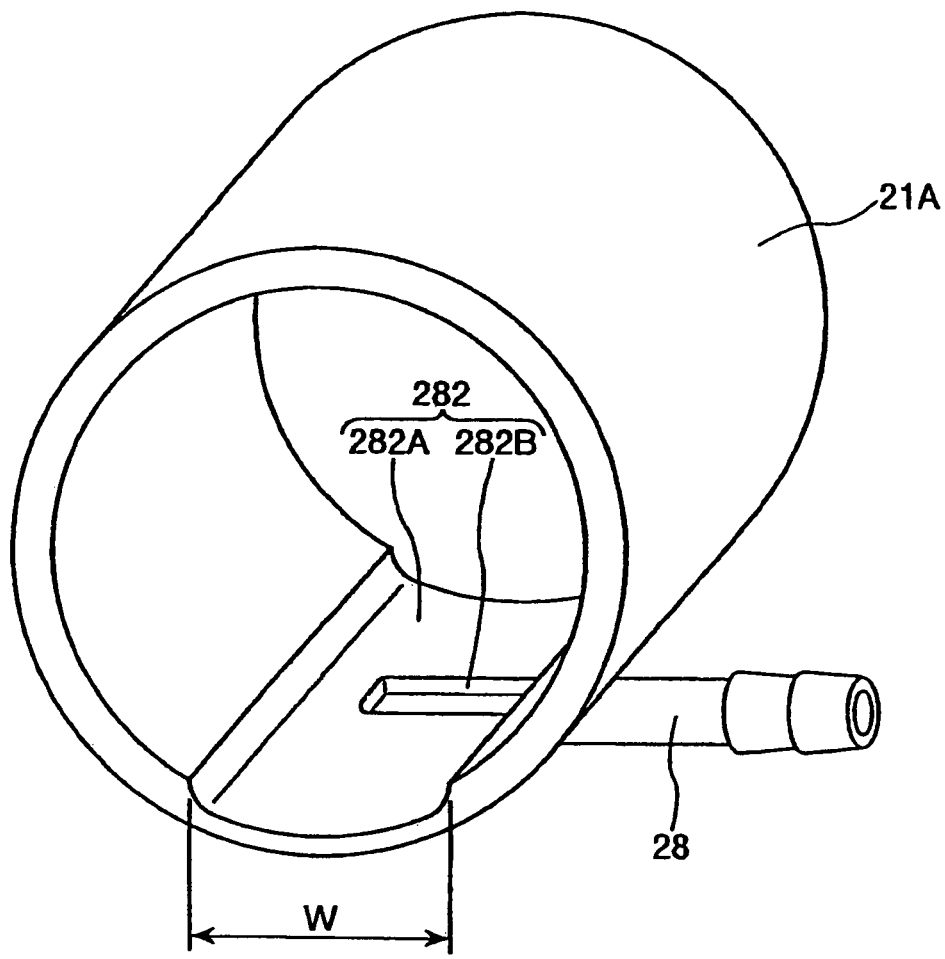
FIG. 9 is a perspective view of the housing used in the oxygenator shown in FIG. 8.

FIG. 8 shows an embodiment in which a part of the housing of the oxygenator possesses a modified shape or configuration. In the embodiment shown in FIG. 8, the housing 21A is provided with a passage enlargement 282. The passage enlargement 282 is comprised of a first enlargement 282A and a second enlargement 282B continuing from the first enlargement 282A. The first enlargement 282A is located on the upstream side of the second enlargement 282B. The first enlargement 282A A is comprised of a recess formed in the inner peripheral surface of the cylindrical housing in a region surrounding the blood outlet port 28 and extending axially along the entire length of the cylindrical housing. In the illustrated embodiment, this recess forming the first enlargement 282A possesses a constant width along the entire axial extent of the housing.

In addition, as can be seen from a comparison of FIGS. 5 and 8, the blood outlet port is moved radially outwardly to thereby form the second enlargement 282B.

By virtue of the passage enlargement, the flow velocity of the blood passing through the filter is reduced, thereby capturing bubbles at the filter with greater ease.

It is to be recognized that the principles, preferred embodiments and modes of operation have been described in the foregoing specification, but the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. An oxygenator comprising:
   a housing;
   a hollow fiber membrane bundle comprised of a plurality of gas-transmissive hollow fiber membranes each possessing a lumen, the hollow fiber membrane bundle comprising an outer peripheral surface defining an outer circumference of the hollow fiber membrane bundle;
   a gas inlet port communicating with the lumens of the hollow fiber membranes to introduce an oxygen-containing gas into the lumens;
   a gas outlet port communicating with the lumens of the hollow fiber membranes;
   a blood inlet port communicating with a blood flow path that is exterior of the hollow fiber membranes in the housing;
   a blood outlet port communicating with the blood flow path;
   a filter member positioned in the housing in surrounding relation to the outer peripheral surface of the hollow fiber membrane bundle;
   the filter member comprising a warp thread and a weft thread, the warp thread and the weft thread both being arranged so as not to be parallel to a plane that is perpendicular to a longitudinal axis of the filter member, and the filter member possessing circumferential elasticity allowing an inner circumference of the filter member to be increased from a natural non-expanded state prior to placement on the hollow fiber membrane bundle to an expanded state in which the inner circumference of the filter member is increased when placed on the hollow fiber membrane bundle by being stretched in a direction about the inner circumference of the filter member; and
   the inner circumference of the filter member in the natural non-expanded state being less than the outer circumference of the hollow fiber membrane bundle.

2. The oxygenator according to claim 1, wherein the outer circumference of the hollow fiber membrane bundle is represented by L1 and the inner circumference of the filter member in the natural non-expanded state is represented by L2, and wherein $0.5 \leq L2/L1 < 1$.

3. The oxygenator according to claim 1, wherein the filter member is made of a material which captures bubbles in the blood passing through the filter member.

4. The oxygenator according to claim 1, wherein the filter member is a mesh.

5. The oxygenator according to claim 1, wherein the filter member is a mesh having a mesh size not greater than 80 μm.

6. The oxygenator according to claim 1, wherein the filter member is hydrophilic.

7. The oxygenator according to claim 1, wherein the filter member is a sheet member rolled into an annular form with opposite edges of the sheet member being joined together along a joint.

8. The oxygenator according to claim 7, wherein the joint extends in a direction inclined relative to a widthwise direction of the filter member so that the joint extends around a portion of the circumference of the filter member, the inclined direction being substantially parallel to an extending direction of the warp thread or the weft thread of the filter member.

9. An oxygenator comprising:
   a housing;
   a hollow fiber membrane bundle positioned in the housing and comprised of a plurality of integrated hollow fiber membranes that are transmissive to gas and that each include a lumen, the hollow fiber membrane bundle possessing an outer peripheral surface;
   a gas inlet and a gas outlet respectively positioned upstream and downstream of the lumens of the hollow fiber membranes;
   a blood inlet and a blood outlet respectively positioned upstream and downstream of a blood passage that is exterior of the hollow fiber membranes; and
   a cylindrically shaped filter member arranged in close contact with the outer peripheral surface of the hollow fiber membrane bundle, the filter member possessing a longitudinal axis and being comprised of a warp thread and a weft thread;
   wherein the filter member possesses circumferential elasticity allowing the filter member to be circumferentially expanded when placed on the hollow fiber membrane bundle by being stretched in a direction about the inner circumference of the filter member;
   the warp thread and the weft thread both being arranged so as not to be parallel to a plane that is perpendicular to a longitudinal axis of the filter member; and
   the inner circumference of the filter member in the natural non-expanded state being less than the outer circumference of the hollow fiber membrane bundle.

10. The oxygenator according to claim 9, wherein the filter member is a mesh.

11. The oxygenator according to claim 9, wherein the filter member is a mesh having a mesh size not greater than 80 μm.

12. The oxygenator according to claim 9, wherein the filter member is hydrophilic.

13. An oxygenator comprising:
   a housing;
   a hollow fiber membrane bundle comprised of a plurality of integrated gas-transmissive hollow fiber membranes each possessing a lumen, the hollow fiber membrane bundle comprising an outer peripheral surface defining an outer circumference of the hollow fiber membrane bundle;
   a gas inlet port communicating with the lumens of the hollow fiber membranes at an upstream side of the lumens to permit an oxygen-containing gas to be introduced into the lumens;
   a gas outlet port communicating with the lumens of the hollow fiber membranes at a downstream side of the lumens;
   a blood inlet port communicating with a blood flow path that is exterior of the hollow fiber membranes in the housing;
   a blood outlet port communicating with the blood flow path;

a filter member positioned in the housing in surrounding relation to the outer peripheral surface of the hollow fiber membrane bundle, the filter member possessing a longitudinal axis;

the filter member being comprised of a warp thread and a weft thread forming a mesh;

the warp thread and the weft thread both being arranged so as not to be parallel to a plane perpendicular to the longitudinal axis of the filter member so that the filter member possesses circumferential elasticity allowing an inner circumference of the filter member to be increased from a natural non-expanded state prior to placement on the hollow fiber membrane bundle to an expanded state in which the inner circumference of the filter member is increased when placed on the hollow fiber membrane bundle by being stretched in a direction about the inner circumference of the filter member; and the outer circumference $L1$ of the fiber membrane bundle being dimensioned relative to the inner circumference $L2$ of the filter member in the natural non-expanded state so that $L2/L1<1$.

* * * * *